United States Patent [19]

Willay et al.

[11] 4,329,136
[45] May 11, 1982

[54] APPARATUS FOR THE AUTOMATIC PREPARATION OF AN X-RAY SPECTROMETRY SAMPLE

[75] Inventors: Gérard Willay, Ars sur Moselle; André Wittmann, Metz, both of France

[73] Assignee: Institut de Recherches de la Siderurgie Francaise (IRSID), St-Germain-en-Laye, France

[21] Appl. No.: 2,782

[22] Filed: Jan. 11, 1979

Related U.S. Application Data

[63] Continuation of Ser. No. 878,762, Feb. 17, 1978, abandoned.

[30] Foreign Application Priority Data

Feb. 21, 1977 [FR] France ................................ 77 05002

[51] Int. Cl.³ ............................................. B28B 17/00
[52] U.S. Cl. .............................. 425/174.8 R; 425/456
[58] Field of Search ................. 425/174.8 R, 155, 447, 425/456; 164/336, 338.1, 338.2

[56] References Cited

U.S. PATENT DOCUMENTS

3,125,780  3/1964  Harrison et al. ............. 425/174.8 R
4,116,598  9/1978  Alexandrov et al. ........ 425/174.8 R

Primary Examiner—John H. Parrish
Attorney, Agent, or Firm—Kurt Kelman

[57] ABSTRACT

An apparatus for the preparation of a sample for X-ray spectrometry comprises a crucible for fusible material, a vessel covering the crucible in a first position and serving to receive cast material from the crucible in a second position, an induction coil wherein the crucible is disposed for simultaneously heating the crucible until the material therein is fused and preheating the vessel covering the crucible, a mobile support mounted for rotation about a horizontal axis extending perpendicularly to the axis of the induction coil, the induction coil being affixed to the support and rotation of the support being capable of agitating the crucible during fusion of the material and for turning the crucible from an upright position wherein the material is fused to a casting position wherein the fused material is cast from the crucible, a casting table below the induction coil, and a sliding ramp connecting the casting table to the mobile support for slidingly guiding the vessel from the first to the second position below the crucible when the crucible is turned into the casting position.

10 Claims, 6 Drawing Figures

FIG_1

FIG_2_

FIG_3_

FIG_4_

FIG_5_

FIG_6_

APPARATUS FOR THE AUTOMATIC PREPARATION OF AN X-RAY SPECTROMETRY SAMPLE

This is a continuation, of application Ser. No. 878,762, filed Feb. 17, 1978 now abandoned.

The present invention comprises an apparatus for the automatic preparation of a sample which may be subjected to analysis, and more particularly to the preparation of samples of non-metallic products destined for analysis by the fluorescence of X-rays.

It is known that the accurate analysis of the composition of products, particularly non-metallic product, by X-ray spectrometry is difficult without a very careful preparation of a sample, with the transformation of the product into a pearl of very homogenous vitreous material by a process of fusion-dilution of the product in a flux so as to have a sample which may be readily manipulated and presents a plane and smooth surface.

This is a serious handicap for the large-scale utilization of X-ray spectrometry, for example for product control, since the manual preparation of the sample takes so long and is difficult to handle. Therefore, it has been proposed to provide automatic apparatus designed to compromise between the two contradictory requirements, i.e. precision and speed. Among the most widely used automatic apparatus, two main types may be distinguished according to the manner in which the material is fused in a crucible: (1) heating by a flame or (2) electric heating by induction in the metallic mass of the crucible.

To the first type belongs an apparatus commercially known as "Claisse Fluxer", in which several pearls may be fused and cast simultaneously. This apparatus comprises a fusion device including a gas burner means disposed about a vertically pivotal support and rotatable about its axis. Arms affixed to the support hold a crucible containing a fusible mixture above each burner and a capsule covers each crucible and is preheated before it serves as a receptacle for the casting. After the burners have been lighted, the device is pivoted and agitation of the crucibles during fusion is assured by a revolving motion similar to shaking by hand. After this is stopped and the device is returned to the upright position, the crucible-cover assembly is turned by rotation of a carrier arm about a horizontal axis until the cover is suspended under the crucible. The fused material is then cast into the cover which becomes a vessel in which the cast material solidifies as a pearl.

This second type of automatic apparatus has been described in the British revue "X-ray-Spectrometry", 1974, Vol. 3, pages 137 to 142. This type of apparatus essentially comprises a fusion device comprised of a vertically disposed induction coil in whose gap a crucible is placed, a casting table including an induction coil plate for preheating the vessel, and a clamping member moving the crucible, after fusion of the material therein, above the vessel for discharging the fused material into the vessel by tilting the crucible. The crucible is supported by a vertical support which is subjected to alternating rotational movements about its axis to agitate the material in the crucible during fusion. A pneumatic system operated by a programmed control assures the movements of all parts necessary for the operation of the apparatus and the proper sequence of all operational stages.

Both known types of apparatus have advantages and disadvantages. The induction heated apparatus provides uniform, silent fusion which may be well controlled. However, a pneumatic control system for agitating and displacing the crucible from its fusion position to the casting position requires not only a complex technology but also a certain noise nuisance for the operator. The gas burner apparatus, on the other hand, permanently maintains the crucible on its carrier arm, as well as the casting vessel which is affixed thereto. Thus, it requires no casting table and pneumatic means for transporting the crucible. On the other hand, the vessel must be disengaged after solidification of the pearl, which involves a manual operation. In addition, fusion by gas burners is very noisy and becomes almost intolerable when several burners are operated at the same time. Furthermore, heating by gas burners is rarely uniform, the operator is subjected to the heat emanating from the burners and the combustion gas must be evacuated.

The production pace of both types of apparatus is slow, i.e. of the order of one pearl produced in eight minutes, which is sometimes not compatible with the requirements of the user.

It is the primary object of the invention to provide an apparatus for the automatic preparation of a sample, which operates rapidly and simply and which has the advantages of both types of known apparatus without involving their respective disadvantages.

The above and other objects are accomplished in accordance with the invention with an apparatus which comprises a crucible for holding fusible material from which the sample is to be taken by casting the material fused therein, a vessel covering the crucible in a first position and serving to receive the cast material from the crucible in a second position, and an induction coil means for simultaneously heating the crucible until the material therein is fused and preheating the vessel covering the crucible. Means for agitating the crucible during fusion of the material and for turning the crucible from an upright position wherein the material is fused to a casting position wherein the fused material is cast from the crucible includes a mobile support mounted for rotation about a horizontal axis extending perpendicularly to the axis of the induction coil means, means for affixing the induction coil means to the support for rotation therewith, and means for imparting rotation to the support. Finally, the apparatus also comprises means permitting the vessel to be placed in the second position below the crucible when the crucible is turned into the casting position, which means includes a casting table disposed below the induction coil means and a sliding ramp connecting the casting table to the mobile support in the region of an upper end of the induction coil means for slidingly guiding the vessel from the first to the second position.

The above and other objects, advantages and features of the present invention will become more apparent from the following detailed description of certain now preferred embodiments thereof, taken in conjunction with the accompanying drawing wherein.

Figure 1:
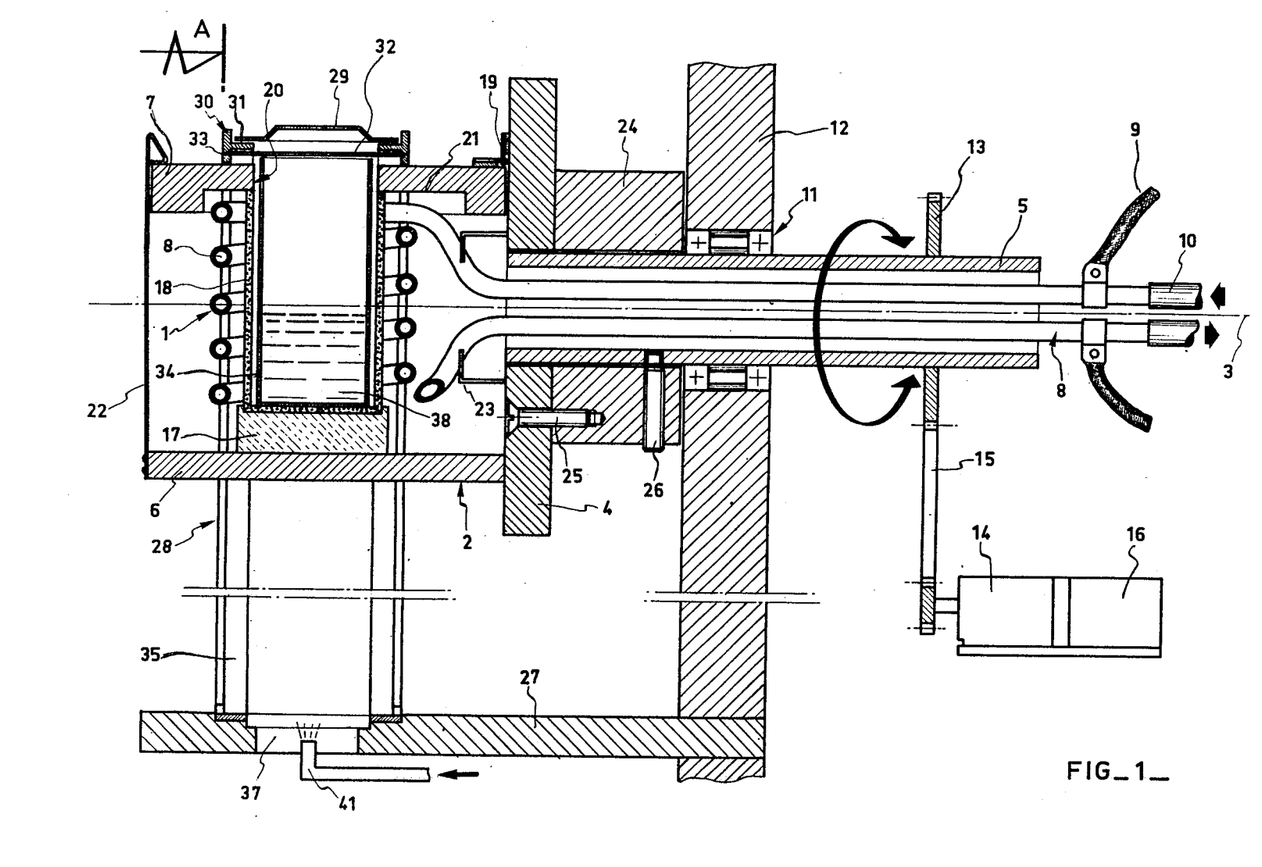
FIG. 1 is a tranverse section in a median plane of the apparatus showing one embodiment of the crucible mounting and sliding ramp.
Figure 2:
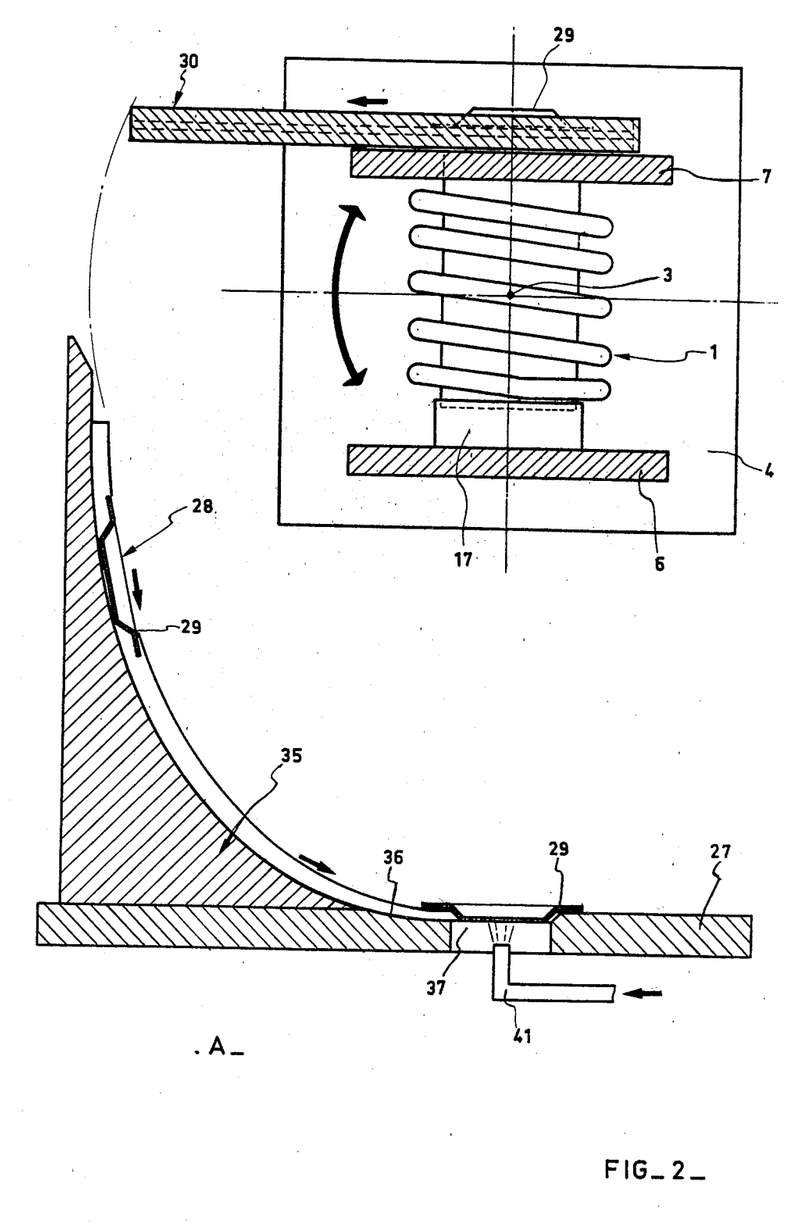
FIG. 2 is an end view in section along plane A—A of FIG. 1.
Figure 3:
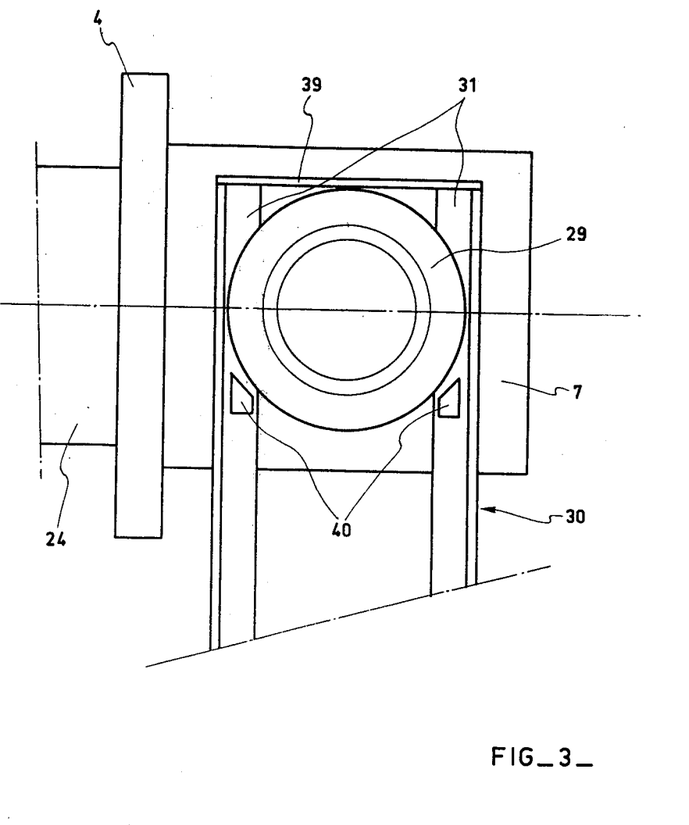
FIG. 3 is a top view illustrating the positioning of the vessel above the induction coil means.

Referring now to the drawing, the same reference numerals designate like parts operating in a like manner in all figures. As shown in FIGS. 1 to 3, the apparatus comprises crucible 34 for holding fusible material 38 from which the sample is to be taken by casting the material fused therein. Vessel 29 covers the crucible in a first position and serves to receive the cast material from the crucible in a second position. Induction coil means 1 is arranged for simultaneously heating crucible 34 until material 38 therein is fused and preheating vessel 29 covering the crucible.

As shown in FIG. 1, the induction coil means comprises an induction coil having a vertical axis and defining a gap wherein crucible 34 is disposed coaxially. The coil has terminal conductor portions 8 connected to a source of high-frequency electric current (not shown) by flexible cables 9. The illustrated solenoid coil consists of copper tubing and the terminal portions of the coil are connected by flexible connector 10 to a source of cooling medium, for instance water, (also not shown) to permit the circulation of the cooling medium through the coil and thus to avoid overheating of the same.

Induction coil means 1 is mounted on mobile support 2 which is mounted for rotation about horizontal axis 3 extending perpendicularly to the axis of the induction coil means. Support 2 is comprised of support element 4 for induction coil means 1, base plate 6 attached to and projecting from support element 4 and supporting crucible 34 within the induction coil means, removable cover 7 hinged to the support element at 19 and disposed above the induction coil means, and tubular shaft 5 supporting support element 4 for rotation about horizontal axis 3 of the shaft. Two clamps 23 affix induction coil means 1 to support 2 for rotation therewith.

The means for imparting rotation to mobile support 2 comprises pinion 13 affixed to tubular shaft 5, motor 14 having an output shaft, transmission chain 15 connecting the pinion to the motor output shaft, and motor control 16 programmed to operate the motor in an operating sequence of agitating and turning crucible 34 in a manner to be described hereinafter.

In the illustrated embodiment, base plate 6 carries socket 17 for protective sleeve 18 whose bottom rests in the socket and which is interposed coaxially between the induction coil and the crucible. Socket 17 and sleeve 18 are of electrically and thermally insulating refractory material, such as silica, and the principal function of sleeve 18 is to avoid too great a lateral heat dissipation.

Cover 7 is disposed in the region of and above an upper end of induction coil 1 and is removable by pivoting the cover about hinge 19. The cover defines port 20 in alignment with the central gap of induction coil 1 and, when closed, its inner face 21 rests on the upper end of sleeve 18, thus pressing the sleeve by its weight against socket 17 and holding the sleeve immobile within the induction coil during operation of the apparatus. The cover is held closed and locked in its closed position by resilient tongue 22 having one end affixed to base plate 6 while an upper hooked end engages cover 7.

Horizontal tubular shaft 5 is journaled in frame 12 by anti-friction roller or ball bearings 11 and displacement of mobile support 2 in relation to frame 12 is avoided by mounting centering member 24 between support element 4 and the frame. This centering member is affixed to support element 4 by an annulus of assembly screws 25 concentrically surrounding horizontal axis 3 and set screw 26 connects the centering member to shaft 5 so as to make the heating furnace integral with the rotary shaft for rotation therewith.

Frame 12 also carries horizontally extending plate 27 disposed below mobile support 2 and which serves as a casting table, as will be explained hereinbelow.

Preferably, all the constituent parts of mobile support 2 are of refractory and electrically insulating material. For instance, we have found a structural material consisting of a mixture of asbestos and refractory cement suitable for the purpose. Such a material will not be damaged by temperatures of the order of 800° C. to 900° C. It is available commercially under the name "Asbestolite".

Sliding ramp 28 connects casting table 27 to mobile support 2 in the region of an upper end of induction coil means 1 for slidingly guiding vessel 28 from the first position, wherein it is disposed atop the induction coil means, to the second position, wherein it is disposed therebelow. In the first position, the vessel is preheated by the induction coil means and the sliding ramp permits the preheated vessel to be placed in the second position on casting table 27 when support 2 is tilted to cast the fused material from the crucible into the vessel. In the illustrated embodiment, the sliding ramp is constituted by two parallel T-rails of metal which are disposed on both sides of port 20 in cover 7 and extend perpendicularly to horizontal axis of rotation 3 of mobile support 2.

As best shown in FIGS. 2 and 3, the illustrated sliding ramp for vessel 29 is comprised of two distinct and successive parts cooperating upon rotational tilting movement of mobile support 2 to provide a continuous sliding support for vessel 29 from the first to the second position. First sliding ramp part 35 forms a lower end of the ramp and is fixed to casting table 27, this arcuate part 28 of the ramp having a vertical upper portion gradually merging into horizontal lower portion 36 leading to cavity 37 in casting table 27 designed to receive and accurately position vessel 29 below crucible 34 at the moment of casting. First ramp part 35 functions like a toboggan. Second sliding ramp part 30 forms an upper end of the ramp and is attached to, and movable with, mobile support 2. As shown, ramp part 30 is affixed to cover 7 in the plane of which it presents a horizontal support surface 31 constituted by the two facing legs of the T-shaped rails and permitting vessel 29 to be placed above induction coil means 1 without contact therebetween. At one end, movable ramp part 30 has end wall 39 whose function will be explained hereinbelow. Ramp part 30 extends rectilinearly and the end opposite to end wall 39 of ramp part 30 is arranged to engage the vertical upper portion of fixed ramp part 35 when support 2 is rotatably tilted at the time of casting (see double-headed arrow in FIG. 2) so that vessel 29 glides from part 30 onto part 35.

As will be seen from FIG. 1, platinum retaining blade 32 extends diametrically across port 20 in cover 7, being held in position in slots 33 defined in the T-rails. This blade serves to retain crucible 34 within the induction coil means in the tilted casting position of the crucible.

When it is desired to prepare a sample in the shape of a pearl for X-ray spectrometric analysis, the apparatus is operated in the following manner:

The non-metallic material to be analyzed is finely crushed and the comminuted material is mixed with a flux, for example anhydrous sodium tetraborate, in a ration of, say, about 200 mg of material to about 4 to 5 g of flux. This mixture is poured into cylindrical crucible 34 which may be of a platinum-gold-rhodium alloy. The crucible holding material mixture 38 is then placed into silica sleeve 18 in the interior of induction coil 1, hinged cover 7 is closed and locked by engaging tongue 22 therewith. This operating position is shown in FIG. 1.

As will be apparent from the drawing, the upper end of crucible 34 extends through port 20 of cover 7 towards or into contact with retaining blade 32. Casting vessel 29, which may be of platinum and has the shape of a dish with a wide rim, is placed with its rim on support surface 31 so that it faces the induction coil means in an inverted position thereabove.

At this point, a high-frequency current of the order of 3 MHz is supplied to the inductin coil through cables 9 and a current of an intensity of about 0.8 A runs through the coil. At the same time, water is circulated through the cooper tubing of the coil to prevent overheating. This begins the heating of the crucible to fuse material 38 therein. During the entire heating process, the crucible is agitated by constant shaking, which may be effected in two ways.

In one mode of agitation, crucible 34 is subjected to oscillations only at one side of its vertical position so that vessel 29 is retained by end wall 39 on support surface 31.

In the other mode of agitation, the crucible is shaken out of its vertical position towards both sides. While, when hot, the surface of the platinum vessel will be rough and thus held by friction on the support surface, it will be preferred as a safety measure to provide additional retention means, such as frangible abutments 40, on support surface 31 to hold vessel 29 in position during shaking. As soon as the tilting angle exceeds a predetermined parameter, i.e. when the rotation of support 2 exceeds the oscillating range used for agitating the crucible during fusion and enters the tilting range used for casting the fused material, the weight of vessel 29 on inclined support surface 31 will break frangible abutments 40 to permit the vessel to slide down inclined ramp part 30.

Whatever the principle of shaking the crucible, its agitation is obtained by a partial rotational movement, either unidirectional or alternating, of mobile support 2 about axis 3, the induction heating means being clamped to the support by clamps 23 and the crucible held coaxially in the induction coil 1. In a manner well known per se and forming no part of the invention, electric control 16 is so programmed as to effectuate the desired rotational movements of shaft 5 sequentially and suitably timed for fusing the material while agitating the crucible and then tilting the crucible for casting the fused material.

The amplitude of the shaking mvoements may be held to relatively small angles to avoid accidental spilling of the fused material from the crucible. Since the latter is usually filled only up to about one tenth of its total volume, an amplitude of about 30° with respect to the vertical is usually satisfactory to obtain good agitation and without incurring the danger of spills. As to the period of the agitating oscillations, values of the order of one second per cycle (unilateral shaking) provide good mixing of the material in the crucible and reduce the forces of inertia in the oscillating assembly. In the case of alternating shaking, the period of oscillations may be about three to four seconds. The total time of agitation is of the order of about two minutes. At the end of about one minute, the material is fused and reaches a temperature of about 1100° C. to 1150° C. After another minute, the continued shaking has homogenized the fused material.

Vessel 29 disposed above induction coil means 1 and crucible 34 is preheated by heat radiation and convection, in addition to eddy currents induced by lines of secondary fields, to reach a temperature of the order of 700° C. to 800° C. which is sufficient for casting. Casting is now effected in the following manner:

After the agitating oscillation has been terminated, the electric current supply to the induction coil is cut and the rotation may be continued at slow speed or may be stopped for several seconds if vessel 29 is too hot, after which the slow rotational tilting movement is continued to permit preheated vessel 29 to slide down ramp part 30 to ramp part 34 whence it slides down to be seated in cavity 37 in casting table 27. This operation requires less than a second and the vessel is put in place before the fused material can pour out of crucible 34. As soon as preheated vessel 29 has been properly positioned on the casting table, support 2 is rapidly turned by about 120° into the casting position of crucible 34, i.e. the crucible is tiled from its upright into the casting position to enable the fused material to be cast into vessel 29. As will be appreciated, the crucible is retained in position by retaining blade 32 when tilted. Furthermore, it will also be seen that crucible 34 projects several millimeters beyond cover 7 to avoid any contact between the cast product and induction coil 1.

The entire casting operation generally lasts about 15 to 20 seconds and proceeds in two phases. The first phase takes about two or three seconds to empty the crucible. In a second phase, which may be timed to last from 0 to 30 seconds, the crucible remains in the tilted position to enable the last drop suspended on the rim of the crucible to cool and solidify on the rim (usually within 10 to 15 seconds). The assembly is then returned to its upright position. During the second phase, a blast of air is directed against vessel 29 from nozzle 41 to cool the fused material in the vessel in the shape of a pearl, the blast of air being actuated, is desired, by closing of a limit switch (not shown) in the path of the tilting assembly. A suitable timing device (also not shown) stops the air blast. The resilient tongue 22 is now disengaged from cover 7 to unlock the same, the cover is removed by pivoting the same about hinge 19, the crucible is removed and replaced by another crucible holding a batch of material. After the pearl as cooled in vessel 29, the vessel is removed and the pearl is recovered therefrom simply by turning the vessel over.

The total preparation time from the introduction of the crucible into the induction coil to the solidification of the pearl does not exceed about three minutes. This is a 60% improvement over the time required by the conventional types of apparatus described hereinabove. This considerable reduction in the preparation time is particularly advantageous when it is desired to analyze samples of slag removed from a steel converter during the steel making process. Since this process is relatively short, results of any such analysis must be available rapidly if they are to be used to change the course of the process.

We believe that the rapidity of preparation with the apparatus of the present invention is due, at least primarily, to the more effective agitation of the crucible during fusion of the material mixture, which permits the time for the fusion to obtain a very homogenous liquid mixture to be reduced. In the known apparatus, the mixture is, in effect, agitated during fusion by centrifugal forces generated by the rotation of the crucible about its axis or an axis parallel thereto. In the apparatus of this invention, on the other hand, agitation of the material mixture is obtained by gravity due to shaking the crucible about an axis perpendicular to its own axis, which causes a better mixing of the material to be analyzed in the mass of the flux.

The apparatus of the invention may be used generally for the automatic preparation of a sample of material to be analyzed where the sample is prepared in a dilution-fusion process. It is particularly useful in the automatic preparation of pearls serving as samples to be analyzed by X-ray spectrometry, i.e. the fluorescence of X-rays, especially of non-metallic materials, such as minerals, rocks, agglomerates, slags, refractories, powders, etc.

Obviously, various structural changes may occur to those skilled in the art without departing from the spirit and scope of this invention and some modified embodiments of specific structural parts of the apparatus will now be described.

For instance, it may be desirable to protect "Asbestolite" cover 7 more effectively from the heat emanating from induction coil furnance 1. For this purpose, refractory sleeve 18 may be passed through port 20 in cover 7, like crucible 34 in FIG. 1, and the sleeve will then be held in place not by engagement with surface 21 of the cover but it will be held in position resiliently by retaining blade 32, in the same manner as the crucible.

Figure 4:
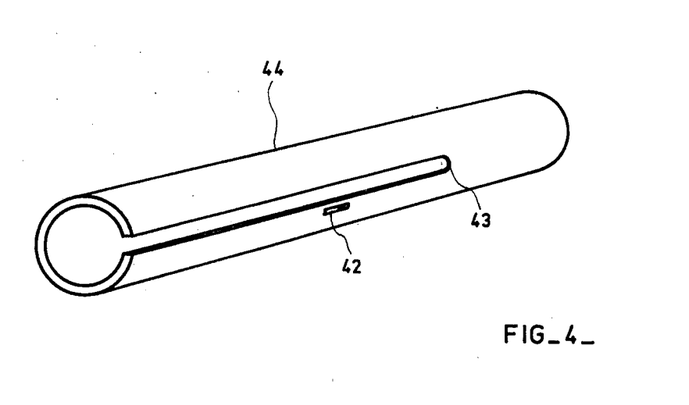
FIG. 4 is a perspective view of one embodiment of a sliding element.
Figure 5:
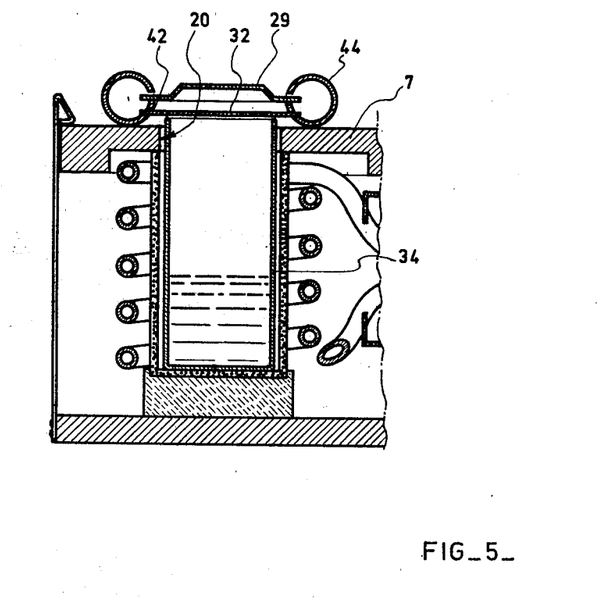
FIG. 5 is a sectional view showing the mounting of the sliding element of FIG. 4 on the cover of the crucible.

Also, for reasons of the hot environment or of risks of electric sparks at the points of contact between vessel 29 and sliding ramp part 30, it may be preferred to avoid use of metal for this part. Therefore, as shown in FIGS. 4 and 5, it may be preferred to use a mobile sliding ramp part of refractory material, the illustrated embodiment showing a pair of tubes 44 of alumina, for example, which are readily available commercially, and which are provided with an elongated slot extending in an axial direction, as shown in FIG. 4. Analogous to slits 33 in the embodiment of FIG. 1, tubes 44 are provided with slits 42 to receive retaining blade 32. The wide rim of vessel 29 is held in the elongated slots of the pair of tubes, as illustrated in FIG. 5, and bottom 43 of the slots in tubes 44 prevents the vessel from being displaced from its preheating position above crucible 34 when the crucible is agitated in a single direction, analogously to end wall 39 in the previously described embodiment. Also as in that embodiment, abutments similar to abutments 40 may be provided to prevent vessel 29 from sliding out of position when bilateral shaking is used.

FIG. 5 shows yet another modification having advantages with respect to heating efficiency and casting conditions. In the previously described embodiment, cylindrical crucible 34 rests in socket 17 during heating, with the bottom of refractory sleeve 18 interposed between the crucible and socket. This mechanical contact may bring about thermal dissipation reducing the heat efficiency. This is avoided according to the embodiment of FIG. 6 by providing means for suspending crucible 34 within sleeve 18 so as to define a thermally insulating space 46 between the bottoms of the crucible and the sleeve, the bottom of the sleeve resting directly on base plate 6. In the illustrated embodiment, the suspending means is comprised of annular collar 45 disposed at an open end of the crucible and supported on the rim of the sleeve. The sleeve, as has been explained hereinabove, extends through port 20 in cover 7 and the diameter of the port is increased so as to accommodate collar 45 when the cover is closed.

Figure 6:
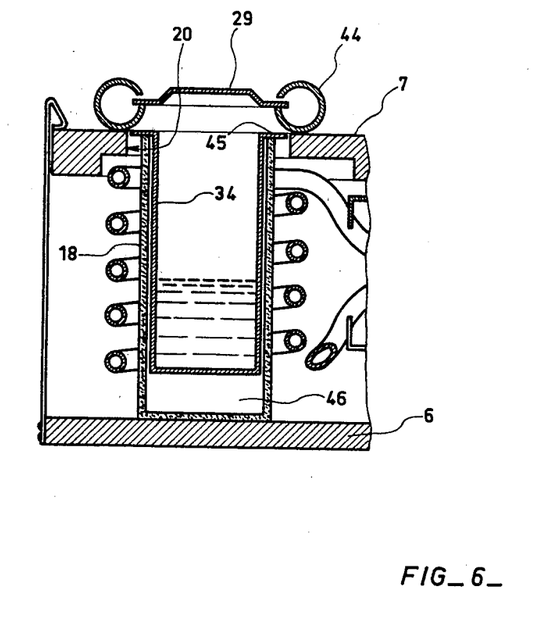
FIG. 6 is a like view showing another embodiment of installing the crucible in the gap of the induction coil means.

This embodiment has not only thermal advantages but also provides an improvement in the casting stage. With the first described embodiments wherein the crucible is retained by blade or strip 32 when it is tilted into the casting position, a drop always remains on the rim of the crucible at the end of the casting. When the crucible is returned into the upright position, this drop runs down the crucible, wets surrounding sleeve 18, and may lodge between the outer wall of the crucible and the inner wall of the sleeve. This may lead to deterioration of the platinum alloy from which the crucible is made. This disadvantage remains even if the operation is so timed that the drop solidifies before the crucible is tilted back. As a matter of fact, such a solidified drop may detach itself once the crucible has resumed its upright position and may lodge itself in the space between the sleeve and the crucible. As soon as heating begins in a subsequent operation, it will then rapidly melt. When the crucible is suspended by annular collar 45, on the other hand, the final drop of fused material will remain on the upper surface of the collar and cannot penetrate into the space between the sleeve and crucible. Furthermore, as will be obvious, a circumferential portion of collar 45 may be shaped into a spout facilitating the pouring of the fused material in the casting stage.

In another modification, among the many possible ones, cavity 37 in casting table 27 may be eliminated, if desired and may be replaced by a retaining stop on the table to hold vessel 29 in the desired casting position vertically below the crucible as it comes sliding down ramp 28. However, a suitable bore will have to be provided in the casting table in front of such a retaining stop to permit nozzle 41 to discharge its blast of air against the vessel.

What is claimed is:

1. An apparatus for the automatic preparation of a sample of a material to be analyzed, which comprises
   (a) a crucible for holding fusible material from which the sample is to be taken by casting the material fused therein,
   (b) an induction coil means for heating the crucible until the material therein is fused, and
   (c) means for agitating the crucible during fusion of the material and for turning the crucible from an upright position wherein the material is fused to a casting position wherein the fused material is cast from the crucible, said means including
      (1) a mobile support mounted for rotation about a horizontal axis extending perpendicularly to the axis of the induction coil means,
      (2) means for affixing the induction coil means to the support for rotation therewith, and
      (3) means for imparting rotation to the support.

2. The apparatus of claim 1, wherein the mobile support is comprised of a support element for the induction coil means, a base plate supporting the crucible within the induction coil means, a removable cover disposed above the induction coil means, and a tubular horizontal shaft supporting the support element for rotation, and further comprising conductor means passing through the tubular shaft for delivering electric current to the induction coil means, the means for imparting rotation to the support being arranged to turn the shaft about its axis.

3. The apparatus of claim 2, wherein the means for imparting rotation to the support comprises a pinion affixed to the tubular shaft, a motor having an output shaft, a transmission chain connecting the pinion to the motor output shaft, and a motor control programmed to operate the motor in an operating sequence of agitating and turning the crucible.

4. The apparatus of claim 1, wherein the induction coil means is hollow to permit circulation of a cooling medium therethrough.

5. The apparatus of claim 1, further comprising a sleeve of refractory material providing heat and electric insulation disposed inside the induction coil means and coaxial therewith, the crucible being mounted within the sleeve.

6. The apparatus of claim 5, further comprising means for suspending the crucible within the sleeve so as to define a thermally insulating space between the bottoms of the crucible and the sleeve.

7. The apparatus of claim 6, wherein the means for suspending the crucible is comprised of a collar disposed at an open end of the crucible and supported on a rim of the sleeve.

8. The apparatus of claim 7, wherein the collar comprises a pouring spout.

9. The apparatus of claim 1, further comprising a vessel covering the crucible in a first position and serving to receive the cast material from the crucible in a second position, the induction coil means being arranged for preheating the vessel while heating the crucible to fuse the material therein, and means permitting the vessel to be placed in the second position below the crucible when the crucible is turned into the casting position, said means including a casting table disposed below the induction coil means and a sliding ramp connecting the casting table to the mobile support in the region of the upper end of the induction coil means for slidingly guiding the vessel from the first to the second position.

10. The apparatus of claim 9, wherein the sliding ramp is comprised of two distinct and successive parts, a first one of the sliding ramp parts forming a lower end of the ramp and being fixed to the casting table, and a second one of the sliding ramp parts forming an upper end of the ramp and being attached to, and movable with, the mobile support, the movable second part cooperating with the fixed first part upon rotational movement of the support to provide a continuous sliding support for the vessel from the first to the second position thereof.

* * * * *